United States Patent [19]

Silvestrini et al.

[11] 4,252,721

[45] Feb. 24, 1981

[54] CYCLOALKYLTRIAZOLES AND PROCESS FOR OBTAINING SAME

[75] Inventors: Bruno Silvestrini; Leandro Baiocchi, both of Rome, Italy

[73] Assignee: Aziende Chimiche Riunite Angelini Francesco A.C.R.A.F. S.p.A., Rome, Italy

[21] Appl. No.: 25,273

[22] Filed: Mar. 29, 1979

[30] Foreign Application Priority Data

Apr. 18, 1978 [IT] Italy .................... 22421 A/78

[51] Int. Cl.³ .......................................... C07D 403/14
[52] U.S. Cl. .............................. 260/243.3; 544/362; 544/366; 424/244; 424/256
[58] Field of Search .................. 544/362, 366; 260/243.3

[56] References Cited

U.S. PATENT DOCUMENTS 3,381,009 4/1968 Palazzo et al. .................... 544/362
3,956,328 5/1972 Irikura .............................. 544/362

*Primary Examiner*—Jose Tovar
*Assistant Examiner*—D. B. Springer
*Attorney, Agent, or Firm*—McGlew and Tuttle

[57] ABSTRACT

Compounds of the general formula:

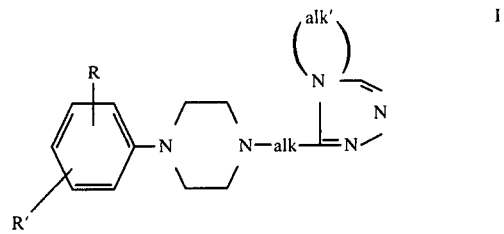

in which alk and alk' represent the bivalent radicals; aliphatic alkyl chains; and R and R' represent the alkyl, halogen, hydrogen, alkyloxy, —OH, —CF₃ or —SCH₃ radicals. Said compounds of the formula I are effective and useful as antiglaucomic and antipsychotic agents and also as additive agents in the withdrawal treatment of various addictive conditions. Methods for their preparation are also disclosed.

9 Claims, No Drawings

CYCLOALKYLTRIAZOLES AND PROCESS FOR OBTAINING SAME

The present invention relates to new compositions useful as antiglaucomic and antipsychotic agents and also useful as additive agents in the withdrawal treatment of patients from the condition of psychophysical dependence from alcohol, smoke or pharmaceutical products. It also relates to new methods of using said new compositions to treat conditions characterized by the hypertensive state of the eye (including glaucoma), delirium, hallucination and other symptoms of the psychosis of the schizophrenic type. The new compositions are also useful in the treatment of the abstinence syndromes in patients with states of psychophysic addiction or dependence to alcohol, smoke and various pharmaceutical products (including narcotic products having analgesic properties). The present invention relates further to new pharmaceutical products which are useful in achievement of the aforementioned objects, as well as to the method for their preparation, and to some new intermediates of said products and to pharmaceutically acceptable salts of the new products. Said new compositions comprise 5-substituted derivatives of the 3,4-cycloalkyl triazoles and are represented by the formula I:

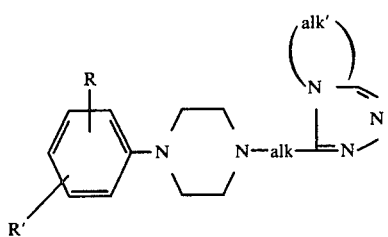

wherein the symbol "alk" represents a linear or branched bivalent aliphatic chain having from 1 to 10 carbon atoms and the symbol alk' represents a linear or branched aliphatic chain having from 1 to 5 carbon atoms; and R and R' (in the cases other than when R=R'=H) each represent two substituents on the aromatic nucleus, which may be the same or different and which may be located in any position on the aromatic ring. Thus the benzene ring in the formula I may be unsubstituted, or may have a substituent in the o, m, or p positions, or may be disubstituted at the om, op, mp, oo positions. In addition, the substituents R and R' may represent alkyl, halogen, alkyloxy, hydroxy, trifluoromethyl, or methylthio. By the term "alkyl" is intended, in particular, a methyl radical and other simple alkyl radicals having up to 5 carbon atoms, such as ethyl, propyl, isopropyl, and the like.

The term "halogen" relates in particular to fluoro and chloro.

The term "alkoxy" refers in particular to methoxy, ethoxy and isopropoxy.

The non-toxic and pharmaceutically acceptable salts of the invention are all those salts known to those skilled in the art which are commonly used to form salts with basic substances to be used as pharmaceutical substances, i.e., salts with monobasic or polybasic mineral acids (hydrochloric, sulfuric, phosphoric, etc.) and salts with monocarboxylic or polycarboxylic organic acids (maleic, lactic, methanesulfonic, acetic, gluconic, pamoic, etc.).

These salts are prepared by conventional techniques beginning with a pharmaceutically acceptable acid and the selected active base.

Some of these salts may be products formed by one or two molecules of acid. In addition, some of these salts may be crystallized both in the anhydrous or hydrated form and, in some cases, may retain one or more molecules of the crystallization solvent.

The compounds of the present invention may be prepared by some alternative methods, which are illustrated in the following schemes:

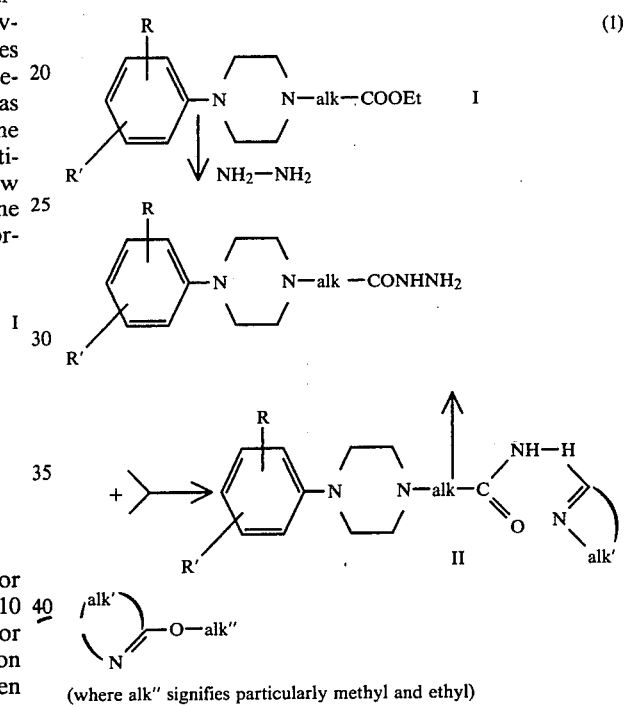

(where alk" signifies particularly methyl and ethyl)

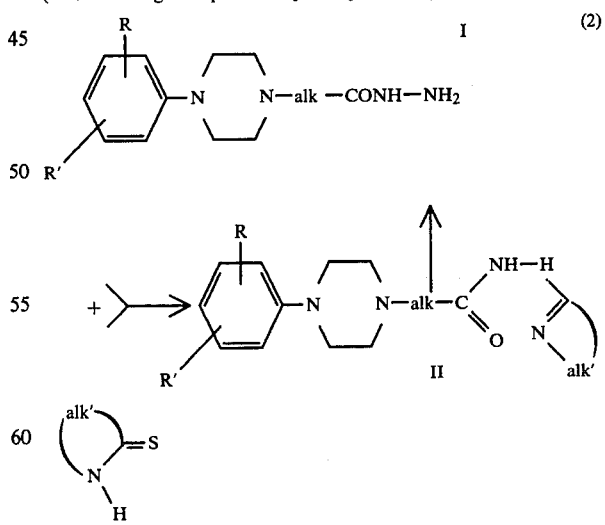

Both of the above-described methods can be applied in the preparation of all the products of the present invention.

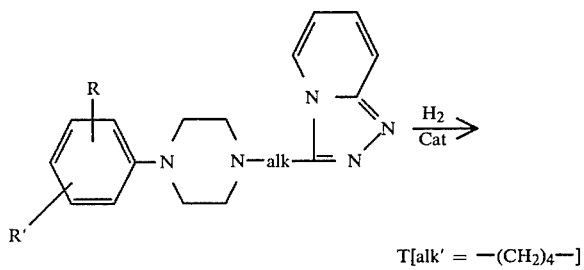

T[alk' = —(CH₂)₄—]

The latter method is only applicable for the preparation of tetrahydro triazole-pyridine derivatives.

In the first of said methods, there are utilized the 4-aryl-piperazinyl-alkanoic esters which are known to those skilled in the art. They are then transformed to the corresponding hydrazides with hydrazine hydrate or, in a homogeneous phase, utilizing a solvent such as ethanol or in a double phase, one of which is aqueous, using catalysts suitable for such reaction.

The hydrazides thus obtained are treated in a suitable solvent at ambient temperatures with an alkyl-lactam. There is obtained the corresponding amidrazone (II) which is separated and cyclized through heating, either in a dry state or in a suitable solvent.

Alternatively, one can conduct two reactions at the same time, by heating directly the hydrazide and the lactam, either in the presence or in the absence of a solvent. In some cases, the presence of a basic catalyst, such as sodium methylate, promotes the speed of the reaction. During the heating, there is first obtained the elimination of alcohol and the formation of the amidrazone, which is not isolated, and, subsequently, the elimination of water with the closure of the triazolic ring. The reaction can be carried out either by removing the alcohol and the water which are formed in the reaction or by carrying out the reaction under reflux conditions.

The desired basic products are separated from the reaction mixture and are then salified using known techniques. In the second method there is utilized, instead of a lactam, its corresponding cyclic thioamide. Even in this case, which proceeds through the formation of hydrogen sulfide rather than alcohol, there is achieved first the formation of the amidrazone, which is not isolated, and then the elimination of water and the closure of the triazolic ring. The third method, which is applicable only in the preparation of the derivatives of 5,6,7,8-tetrahydro-s-triazolo[4,3-a]pyridine, begins with a 4-aryl-piperazinyl-alkanoic acid and with 2-hydrazino-pyridine. Both the 2-hydrazino-pyridine and the 4-aryl-piperazinyl-alkanoic acids are known to those skilled in the art. The two components are heated in the absence of solvent, eliminating the water which is formed during the reaction. The s-triazolo[4,3-a]-pyridine thus obtained is reduced with a selective catalyst which permits the introduction of 4 hydrogen atoms in the pyridyl ring, without removing any of the eventual substituents on the benzene ring. A catalyst which in some cases has proven to be useful in said reaction is palladium-carbon.

The following examples are illustrative of the invention.

EXAMPLE 1

Preparation of 3-[3-[4-(2-tolyl)-1-piperazinyl]propyl]-5,6,7,8-tetrahydro-s-triazol[4,3-a]pyridine (I alk=—(CH₂)₃—; alk'=—(CH₂)₄—; R=2—CH₃; R'=H)

A mixture of 26 g (0.147 mols) of 1-(2-tolyl)piperazine, 23 g (0.154 mols) of ethyl 4-chlorobutyrate, 11 g (0.104 mols) of anhydrous sodium carbonate and 130 ml of absolute ethanol are heated under reflux conditions, with stirring, for 24 hours.

The reaction mixture is cooled to room temperature and the sodium chloride which has been formed is removed by filtration. From the filtrate there is eliminated the alcohol by heating under reduced pressure and the oily residue is distilled. There are obtained 20 g (47%) of the ethyl ester of 4-(2-tolyl)-piperazinylbutyric acid of b.p. of 185° (0.6 mm/Hg), which are dissolved in 50 ml of absolute ethanol. To this solution there is added 15 g of hydrazine hydrate (99%) and the resulting solution is refluxed for 4 hours. The alcohol is then removed under reduced pressure and the residue is taken up with 50 ml solution of 50% potassium carbonate.

The gummy residue, on standing, becomes a filtrable solid of low melting point, which is collected and washed with water and ether (14 g—74%). A small portion is transformed in the hydrochloride which shows a m.p. of 202° C. after crystallization from absolute ethanol. 14 g (0.05 mols) of the above hydrazide is mixed with 6 g (0.05 mols) of O-methylvalerolactam, there are added 0.4 g of dry sodium methylate and the mixture is heated, with stirring, at 120°–130° for 45–50 minutes. The mixture is cooled, and taken up in absolute ethanol. The insoluble impurities are removed by filtration and the filtrate is treated with an excess of a hydrochloric acid solution in ethanol. The precipitate which is formed is removed by filtration and recrystallized from ethanol at 95°; m.p. 266° C.; yield 16 g (73%). On analysis, the product shows the formula $C_{20}H_{29}N_5 \cdot 2HCl \cdot H_2O$.

EXAMPLE 2

Preparation of 3-[2-[4-(2-tolyl)-1-piperazinyl]ethyl]-6,7,8,9-tetrahydro-5H-s-triazol[4,3-a]azepine (I alk=—(CH₂)₂—; alk'=—(CH₂)₅—; R=2—CH₃; R'=H)

(a) Hydrazide of the 4-(2-tolyl)-piperazinyl-propionic acid

A solution of 28.4 g (0.103 mols) of the ethyl ester of 4-(2-tolyl)-piperazinyl-propionic acid and 25 g (0.5 mols) of hydrazine hydrate (99%) in 50 ml of ethanol is refluxed for 5 hours. At the end of the heating cycle the solution is cooled, it is diluted with three volumes of water and the solid hydrazide product which separates is removed by filtration and recrystallized from ethyl acetate. Yield 13.8 g (51%); m.p. 138°–139° C.

The analysis of the hydraxide product indicated the formula $C_{14}H_{22}N_4O$.

(b) A mixture formed by admixing 4.3 g (0.034 mols) of o-methylcaprolactam, 9 g (0.034 mols) of the preceding hydrazide product from (a) and 0.9 g of sodium methylate is heated, with vigorous stirring, by means of an oil bath kept at 160°–170° C. for one hour and fifteen minutes. After cooling there is extracted from the resultant residue the portion soluble in boiling hexane by means of three successive washings and decantations. The hexane extracts are combined and evaporated to dryness. The residue is dissolved in ether and there is added to it a double-equivalent quantity of a solution of hydrochloric acid in ether. The dihydrochloride which precipitates is collected by filtration and recrystallized from ethanol; m.p.

252° C.; yield 11 g (77.5%). The analysis is in agreement with the formula $C_{20}H_{29}N_5.2HCl$.

EXAMPLE 3

Preparation of 3-[2-[4-(2-tolyl)-1-piperazinyl]-ethyl]-5,6,7,8-tetrahydro-s-triazol-[4,3-a]pyridine. (I alk=—$(CH_2)_2$—; alk'=—$(CH_2)_4$—;R=2—$CH_3$; R'=H)

A mixture of 23.1 g (0.22 mols) of o-methyl valerolactam, 52.4 g (0.19 mols) of the hydrazide of 4-(2-tolyl)-piperazinyl-propionic acid and 200 ml of xylene are heated under reflux conditions removing the resultant products, alcohol and the water with a suitable apparatus which products are formed by means of azeotropic distillation. When the formation of water stops (approximately 8 hours), the resulting solution is allowed to cool and the solid which is formed is removed by filtration, washed with hexane and air dried. Yield: 41.5 g (67%); m.p. 158°-160° C. The values of the elemental analysis are in accordance to the elemental formula $C_{19}H_{27}N_5$.

Monochlorohydrate

To a solution of 3.25 g of the aforementioned base in 20 ml of absolute ethanol there is added 2 ml of a 5 N solution of HCl in ethanol. The solution is diluted with an equal volume of ethyl acetate, the solid which separates is removed by filtration and is recrystallized from absolute alcohol. Yield 3.1 g; m.p. 206°-207° C. The analysis of the chlorine ion is in agreement with the formula $C_{19}H_{27}N_5.HCl$.

Dichlorohydrate

To a solution of 3.25 of the base described above, dissolved in 20 ml of absolute ethanol, there is added 4 ml of an ethanolic solution of HCl (5 N). The resultant solid which separates is filtered and recrystallized from absolute ethanol. Yield 3.2 g, m.p. 253°-254° C.

The analysis agrees with the formula $C_{19}H_{27}N_5.2HCl$.

If the same chlorohydrate is recrystallized from alcohol at 95°, there is obtained 3.0 g of product, m.p. 214°-215° C., the analysis of which corresponds to the formula $C_{19}H_{27}N_5.2HCl.H_2O$.

Maleate

A solution obtained by dissolving 3.25 g of the aforementioned base in 20 ml of absolute ethanol is admixed with a solution of 1.16 g of maleic acid in 10 ml of absolute ethanol. The solution is diluted with 30 ml of ethyl acetate and the solid which separates therefrom is collected by filtration and recrystallized from absolute alcohol.

Yield: 2.5 g; m.p. 153°-154° C.

The analysis is in accordance with the formula $C_{19}H_{27}N_5.C_4H_4O_4$.

EXAMPLE 4

Preparation of 3-[2-[4-(3-chlorophenyl)-1-piperazinyl]-ethyl]-5,6,7,8-tetrahydro-s-triazol[4,3-a]pyridine. (I alk=—$(CH_2)_2$—; alk'=—$(CH_2)_4$—; R=3—Cl, R'=H)

(a) Preparation of hydrazide of the 4(3-chlorophenyl)-piperazinyl-propionic acid.

A solution of 14 g (0.048 mols) of the ethyl ester of 4-(3-chlorophenyl)-piperazinyl-propionic acid and 12.5 g (0.25 mols) of hydrazine hydrate (99%) in 20 ml of ethanol is refluxed for 4 hours.

From the final solution the alcohol is removed under reduced pressure, and the residue is taken up with water and the oil which separates is extracted with chloroform. The residue which is obtained when the chloroform is removed is recrystallized from an hexaneethyl acetate mixture.

Yield: 13 g (98%); m.p. 110°-112° C.

The elemental analysis results in agreement with the formula $C_{13}H_{19}ClN_4O$.

(b) A mixture of 2.5 g (0.022 mols) of 2-thiopiperidone, 5.4 g (0.019 mols) of the above hydrazide and 0.1 g of dry sodium methylate are heated, with stirring, at 120°-130° C. for 4 hours.

At the end of the heating period, the residue is taken up in water, the solid thus obtained is filtered and, after air drying, is dissolved in absolute alcohol. To this solution there is added an excess of an ethanolic HCl solution and the solid which precipitates is collected by filtration and recrystallized from absolute ethanol.

Yield: 6 g (75%); m.p. 211° C.

The elemental analysis indicates a formula of $C_{18}H_{24}ClN_5.2HCl$

EXAMPLE 5

Preparation of 3-[2-[4-(2-tolyl)-1-piperazinyl]-ethyl]-5,6,7,8-tetrahydro-s-triazol-[4,3-a]pyridine (I alk=—$(CH_2)_2$—; alk'=—$(CH_2)_4$—; R=2—$CH_3$; R'=H)

(a) Hydrazide of the 4-(2-tolyl)-piperazinyl-propionic acid with the 3,4,5,6-tetrahydro-2-hydrazino-pyridine.

To a solution of 8 g (0.07 mols) of O-methyl-valerolactam in 120 ml of benzene there is added 17.5 g (0.067 mols) of hydrazide of the 4-(2-tolyl)-piperazinyl-propionic acid. The suspension is vigorously stirred for 3 hours at room temperature.

The resulting solid is collected by filtration and washed with benzene. Yield: 20 g (87%); m.p. 110° C. with decomposition (preheated bath).

The elemental analysis agrees with the empirical formula $C_{19}H_{29}N_5O$.

(b) 18 g (0.053 mols) of the above amidrazone are suspended in 200 ml of benzene. The mixture is refluxed for 3 hours, removing azeotropically the water which is formed. At the end of heating cycle the mixture is cooled, the solid which is formed is removed by filtration and recrystallized from benzene. Yield: 15 g (88%); m.p. 161°-162° C.

The elemental analysis agrees with the empirical formula $C_{19}H_{27}H_5$.

EXAMPLE 6

With one of the methods described in Examples 1-4 there have been prepared:

3-[2-[4-(2.5-dichlorophenyl)-1-piperazinyl]-ethyl]-6,7,8,9-tetrahydro-5H-s-triazol[4,3-a]azepine (I alk=—$(CH_2)_2$—; alk'=—$(CH_2)_5$—; R=2—Cl; R'=5 Cl)

Monochlorohydrate. $H_2O$ m.p. 220° C. (from alcohol at 95° C.) The hydrazide of the 4-(2.5-dichlorophenyl)-piperazinyl-propionic acid, necessary for the synthesis of said product, was prepared by the previously described method, and has a m.p.=135°-137° C. (from ethyl acetate).

The elemental analysis shows a formula of $C_{13}H_{18}Cl_2N_4O$. The ethyl ester of the 4-(2.5-dichlorophenyl)-piperazinyl-propionic acid, necessary for the synthesis of the preceding hydrazide, was prepared by the described method and has a b.p. of 198°–200° C./1 mm.

The elemental analysis shows a formula of $C_{15}H_{20}Cl_2N_2O_2$.

3-[2-[4-(2.5-dichlorophenyl)-1-piperazinyl]-ethyl]-5,6,7,8-tetrahydro-s-triazol[4,3-a]pyridine (I alk=—$(CH_2)_2$—; alk'=—$(CH_2)_4$—; R=2-Cl; R'=5 Cl)

Dichlorohydrate. $H_2O$ m.p.=218° C. (from alcohol at 95° C.)

3-[2-[4-(3-chlorophenyl)-1-piperazinyl]-ethyl]-6,7,8,9-tetrahydro-5H-s-triazol[4,3-a]azepine (I alk=—$(CH_2)_2$—; alk'=—$(CH_2)_5$—; R=3—Cl; R'=H)

Chlorohydrate m.p. 234° C. (from absolute ethanol)

3-[3-[4-(2-tolyl)-1-piperazinyl]-propyl]-6,7,8,9-tetrahydro-5H-s-triazol-[4,3-a]azepine. (I alk=—$(CH_2)_3$—; alk'=—$(CH_2)_5$—; R=2—$CH_3$; R'=H)

Monochlorohydrate m.p. 271° C. (from absolute ethanol).

3-[2-[4-(2-methoxyphenyl)-1-piperazinyl]-ethyl]-6,7,8,9-tetrahydro-5H-s-triazol[4,3-a]azepine (I alk=—$(CH_2)_2$—; alk'=—$(CH_2)_5$—; R=2—$OCH_3$; R'=H)

Monochlorohydrate m.p. 230° C. (from absolute ethanol).

EXAMPLE 7

Preparation of 3-[2-[4-(2-tolyl)-1-piperazinyl]-ethyl]-5,6,7,8-tetrahydro-s-triazol[4,3-a]pyridine (I alk=—$(CH_2)_2$—; alk'=—$(CH_2)_4$—; R=2—$CH_3$; R'=H) by the reduction of the 3-[2-[4-(2-tolyl)-1-piperazinyl]-ethyl]-s-triazol[4,3-a]pyridine.

(a) Preparation of the 4-(2-tolyl)-piperazinyl-propionic acid.

31 g (0.135 mols) of 4-(2-tolyl)piperazinyl propionitrile are dissolved in a solution of 8.4 g (0.150 mols) of KOH in 250 ml of 60% ethanol. The solution is refluxed for 4 hours and the ethanol is then removed under reduced pressure. The residual aqueous solution is washed with ether and treated with 25 ml of 6 N HCl.

There is thus precipitated the chlorohydrate of the 4-(2-tolyl)-piperizinyl-propionic acid which is collected by filtration, washed with water and air dried. Yield: 28.9 g (74%); m.p. 232° C.

20 g (0.071 mols) of the above chlorohydrate are suspended in 80 ml of water, there are added 3.4 g (0.085 mols) of NaOH in pellet form and the mixture is stirred at room temperature for one hour.

The solid which forms is collected by filtration, washed with water and air dried. The m.p. of the product is 90° C.

(b) Preparation of the 3-[2-[4-(2-tolyl)-1-piperazinyl]-ethyl]-s-triazol-[4,3-a]pyridine.

85.0 g (0.34 mols) of 4-(2-tolyl)piperazinyl-propionic acid and 35.0 g (0.32 mols) of 2-hydrazino-pyridine are heated with stirring for 3 hours at 160° C.

At the end of the heating cycle, the resulting mass is diluted with water and the mixture thus obtained is extracted with ethyl ether. To the ether solution, after drying over sodium sulfate, there is added an excess of ethanolic HCl. The resulting chlorohydrate which precipitates is collected by filtration and recrystallized from absolute alcohol. Yield: 81.0 g (65%); m.p. 255° C.

The elemental analysis indicates the structure $C_{19}H_{23}N_5 \cdot 2HCl$.

(c) A solution of 15 g (0.038 mols) of the above chlorohydrate, dissolved in 750 ml of ethanol at 95° C. is hydrogenated in a Parr shaker at an initial pressure of 3 atmospheres using 1.5 g of a palladium-carbon catalyst.

After 20 hours, the catalyst is removed by filtration, the alcohol is removed and the residue is recrystallized from alcohol at 95°.

The melting point of the product is 216°–218° C., even when mixed with a sample of the dichlorohydrate monohydrate obtained according to Example 3. Yield: 13 g (82%).

EXAMPLE 8

As indicated above, the compounds of the present invention, administered in effective amounts, are effective in treating:

(a) the hypertensive states of the eye, including glaucoma, when administered topically or systemically;

(b) psychopathological symptoms of the psychosis of the schizophrenic type, with particular reference to the hallucinations and to the delirium, by means of oral or parental administration; and (c) abstinence syndromes in patients with states of psychophysical addiction or dependence produced by alcohol, smoke or pharmaceutical substances, by means of oral or parental administration.

In the latter states (c) there is not realized a substitutive treatment for other forms of treatment presently used, but the abstinence syndrome is alleviated by acting on the physiological mechanisms which cause it. The present compounds, therefore, may be considered as adjuvant or supplemental agents which may be used in conjunction with other forms of therapy, such as psychotherapy, in order to facilitate the withdrawal process.

The therapeutic value of the compounds of the present invention for each of the utilities described has been determined by the use of experimental models apt to demonstrate the effect on each of the various symptoms indicated above. The ability to reduce the ocular pressure has been studied both in the normal rabbit, utilizing experimental conditions already described (Burberi et al., "Effects of systemically administered drugs on intraocular pressure in rabbits," Arzneim. Forsch., 20, 1143–1147 (1970); De Feo et al., "Effects of topically instilled drugs on intraocular pressure in rabbits," Arnzeim. Forsch., 25, 806–809 (1975)) and in animals with ocular hypertension.

An example of ocular hypertension used in the tests is that which has been obtained by introducing repeatedly in one of the two eyes of rabbit a suspension of betametasone. It is thus possible to obtain a stable ocular hypertension which cannot be distinguished from the human glaucoma.

The test products have been shown to reduce the ocular pressure in the normal rabbit and in the rabbit with ocular hypertension, both when administered topically, in the form of eye wash at 0.25–0.5% concentration, and when administered parentally at doses between 0.1–1 mg/kg i.v.

In the ocular hypertension the products have been compared to the pilocarpine, in the form of eyewash in 0.5–1% concentration and have proven to be equally active. With respect to the latter product, however, they have the advantage of not producing miosis and other irritations.

In addition, the products have shown an activity similar to that of the neuroleptics in the common laboratory test used for the studies of this class of pharmaceuticals.

By way of example of the methods used, it may be cited that of the amphetamine toxicity in mice (Lagerspetz et al., "Amphetamine toxicity in genetically aggressive and non-aggressive mice," J. Pharm. Pharmacol., 23, 542 (1971)). The products have been compared with chlorpromazine and have shown an activity similar to the latter.

With respect to the latter and to the other traditional neuroleptic agents, the products of the present invention present two basic advantages consisting of the lower toxicity and of the lack of catathony.

On the basis of said last indication, the present compounds may be considered free of the side effects of the extrapyramidal type which, on the other hand, are a common characteristic of the other neuroleptics.

Finally, the tests which have led to the use of the present compounds in the treatment of the addition or habituation to alcohol, to the smoke and to some habit-forming pharmaceuticals substances have been conducted utilizing a completely new operational theory.

It is known that the addition or the dependence to alcohol or to other substances are considered manifestation of psychological adaptations which the organism develops to compensate the depressing effects of said agents.

When the administration of the latter is interrupted, the adaptations effected by the organism are no longer counterbalanced by the opposite effects of said agents and consequently there appear the symptoms of the withdrawal reaction.

As is known, the withdrawal reaction presents itself, in fact, with symptoms of hyperhexitability, muscular tension and tremors, excitation, insomnia and, in the more serious cases, convulsions. For these tests there has been utilized a work theory which considers that, on the base of the phenomena of addiction and of dependence, and, consequently, of the abstinence syndrome, there is a common physiological mechanism which the organism utilizes to adapt itself to a variety of different agents, such as smoke, alcohol, narcotic analgesics, etc.

To verify this theory there has been produced in the animal a syndrome of addiction or dependence to the following substances: alcohol, nicotine, morphine and clonidine. The results obtained show that the abstinence syndromes which result when the above treatments are interrupted may be treated not only with alternate treatments which vary from case to case (i.e., the lobeline is active only in the case of the nicotine, while the methadone is active only in the case of the morphine), but also with substances which act non-specifically in all the above-mentioned types of abstinence syndromes. These latter substances are those claimed in the present invention and are the only ones, in the ambit of the numerous products studied, which possess this property. They may thus be utilized as supplemental agents in the withdrawal treatment of patients with addition or dependence of various natures utilizing a totally new mode of action.

In fact, they seem to act on a physiological system which the organism uses to counterbalance the depressing effect of substances such as the alcohol and the morphine. In this manner it is possible to fight the abstinence symptoms not through substitutive therapy, which often is equally dangerous as the agent which has produced the addiction (such as in the case of methadone used in the treatment of addiction to morphine or to other drugs), but acting directly on the physiological system which is responsible for the abstinence syndrome.

The therapeutic treatments follow the following regime of use: orally, the products are administered at a medium dosage of 25–50 mg three times a day. In the treatment of schizophrenia and other psycotic forms, as well as in the treatment of particularly serious abstinence syndromes, the dosages used may reach 200 mg three times a day.

For the oral administration, there may be used any type of oral formulation, non toxic, commonly used, such as solutions, suspensions, tablets, capsules, powders, show-release formulations and the like.

For parental administration, the products may be administered at the medium dosage of 25–50 mg, 2 or 3 times a day.

In the treatment of glaucoma and of other hypertensive ocular forms the products are administered in the form of eyewash (concentration 0.25–0.5%) from 2 to 4 times a day. To this effect there may be utilized an aqueous or oily formulation chosen among those which are commonly used in the optical field.

In addition, the compounds of the present invention may be administered at the same time with other pharmaceutical agents, bearing in mind the particular type of disease being treated.

What is claimed is:

1. A compound of the formula:

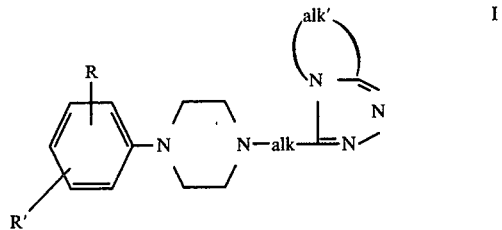

wherein "alk" is selected from the group consisting of linear and branched divalent alkene chains having from 1 to 10 carbon atoms; "alk'" is selected from the group consisting of linear and branched divalent alkene chains having from 1 to 5 carbon atoms; and each R and R' is selected from the group consisting of hydrogen, alkyl having from 1 to 5 carbon atoms, halogen, alkyloxy having from 1 to 3 carbon atoms, hydroxy, trifluoromethyl and methylthio.

2. A compound according to claim 1, consisting of the pharmaceutically acceptable non-toxic acid addition salt of formula I.

3. The compound according to claim 1, consisting of 3-[3-[4-(2-tolyl)-1-piperazinyl]propyl]-5,6,7,8-tetrahydro-s-triazol[4,3a]pyridine.

4. The compound according to claim 1, consisting of 3-[2-[4-(2-tolyl)-1-piperazinyl]ethyl]-6,7,8,9-tetrahydro-5H-s-triazol[4,3a]azepine.

5. The compound according to claim 1, consisting of 3-[2-[4-(2-tolyl)-1-piperazinyl]-ethyl]-5,6,7,8-tetrahydro-s-triazol-[4,3-a]pyridine.

6. The compound according to claim 1, consisting of 3-[2-[4-(3-chloro-phenyl)-1-piperazinyl]-ethyl]-5,6,7,8-tetrahydro-s-triazol-[4,3-a]pyridine.

7. The compound according to claim 1, consisting of 3-[2-[4-(2-tolyl)-1-piperazinyl]-propyl/-6,7,8,9-tetrahydro-5H-s-triazol-[4,3-a]azepine.

8. The compound according to claim 1, consisting of 3-[2-[4-(2,5-di-chlorophenyl)-1-piperazinyl]-ethyl]-6,7,8,9-tetrahydro-5h-s-triazol[4,3-a]azepine.

9. The compound according to claim 1, consisting of 3-[2-[4-(2-methoxyphenyl-1-piperazinyl]-ethyl]-6,7,8,9-tetrahydro-5H-s-triazol[4,3-a]-azepine.

* * * * *

UNITED STATES PATENT AND TRADEMARK OFFICE

CERTIFICATE EXTENDING PATENT TERM
UNDER 35 U.S.C. 156

Patent No.    : 4,252,721

Dated         : February 24, 1981

Inventor(s)   : Bruno Silvestrini et al

Patent Owner  : Aziende Chimiche Riunite Angelini Francesco, A.C.R.A.F. S.p.A.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of 1,411 DAYS with all rights pertaining thereto as provided by 35 U.S.C. 156 (b).

I have caused the seal of the Patent and Trademark Office to be affixed this 30th day of December 1991.

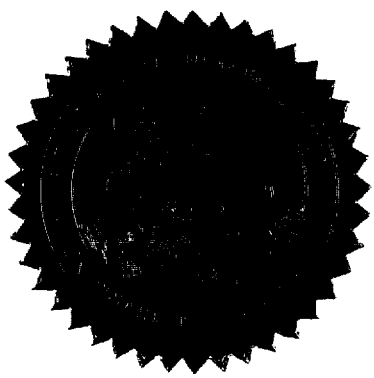

Harry F. Manbeck, Jr.
Assistant Secretary and Commissioner of Patents and Trademarks